United States Patent [19]

Vanderveen

[11] Patent Number: 5,219,331
[45] Date of Patent: Jun. 15, 1993

[54] PUMPING SYSTEM FOR INTRAVENOUS ADMINISTRATION OF A SECONDARY TREATMENT FLUID

[75] Inventor: Timothy W. Vanderveen, Poway, Calif.

[73] Assignee: IMED Corporation, San Diego, Calif.

[21] Appl. No.: 697,249

[22] Filed: May 7, 1991

[51] Int. Cl.⁵ ............................................. A61M 5/14
[52] U.S. Cl. ........................................ 604/81; 604/82; 604/132
[58] Field of Search ............ 604/49, 53, 65, 67, 604/80–85, 132–133, 151–153, 246, 250–251, 410; 128/DIG. 12

[56] References Cited

U.S. PATENT DOCUMENTS

| | | | |
|---|---|---|---|
| 3,756,459 | 9/1973 | Bannister et al. | 222/1 |
| 4,237,881 | 12/1980 | Beigler et al. | 604/65 X |
| 4,397,639 | 8/1983 | Eschweiler et al. | 604/153 |
| 4,533,347 | 8/1985 | Deckert | 604/81 |
| 4,563,173 | 1/1986 | Ledley | 604/81 |
| 4,608,042 | 8/1986 | Vanderveen et al. | 604/81 |
| 4,634,430 | 1/1987 | Polaschegg | 604/141 |
| 4,741,736 | 5/1988 | Brown | 604/134 |
| 4,968,301 | 11/1990 | di Palma et al. | 604/132 |
| 5,000,739 | 3/1991 | Kulisz et al. | 604/132 |
| 5,078,699 | 1/1992 | Haber et al. | 604/250 |
| 5,090,963 | 2/1992 | Gross et al. | 604/132 |

FOREIGN PATENT DOCUMENTS

0361662A1 8/1989 European Pat. Off. .
0432425A1 10/1990 European Pat. Off. .

Primary Examiner—C. Fred Rosenbaum
Assistant Examiner—Corrine Maglione
Attorney, Agent, or Firm—Nydegger & Associates

[57] ABSTRACT

A pumping system is provided for administering a secondary treatment fluid to a patient intravenously in cooperation with a primary treatment fluid administration set already in place. The system includes a self-contained pumping unit having a pumping chamber and a secondary treatment fluid reservoir integral therewith. A secondary fluid line extending from the unit merges with a primary fluid line at a fitting for delivery of the fluids carried in the primary and secondary lines to the patient via a combined IV line.

12 Claims, 3 Drawing Sheets

PUMPING SYSTEM FOR INTRAVENOUS ADMINISTRATION OF A SECONDARY TREATMENT FLUID

FIELD OF THE INVENTION

The present invention pertains to IV administration sets which are useful for infusing treatment fluids to a patient. More particularly, the present invention pertains to a secondary treatment fluid administration set which operates in cooperation with a primary treatment fluid administration set. The present invention is particularly, but not exclusively, useful for the IV infusion of fluid from the secondary set which is controllable independent of the primary set.

BACKGROUND OF THE INVENTION

Intravenous (IV) administration sets which are useful for infusing medical treatment fluids to a patient are well known and widely used. In the most simple configuration, an IV administration set includes a fluid source, an IV line connecting the fluid source to the patient, and a device operatively associated with the IV line to influence the rate of fluid flow to the patient. In more advanced configurations, two sets are placed side by side to deliver two different medical fluids to the patient intermittently.

One such dual delivery system is conventionally termed a "piggyback" system wherein a primary set delivers a primary fluid and a secondary set delivers a secondary fluid to the patient sequence. The source of both the primary and secondary fluids, e.g. bags or bottles, are hung above the patient and linked to the patient by a network of tubing and valves which culminate in a common IV line to the patient. The primary and secondary fluid sources are positioned at a height differential so that delivery of one fluid is favored over the other, thereby imposing a pattern of sequential fluid delivery on the system.

The piggyback system may also include a device which regulates the rate of fluid flow to the patient. Flow rate control devices for the piggyback system are characterized as either pumps or controllers. Controllers rely on gravity for the flow of fluid through the system, while pumps exert an electro-mechanical force on the fluid to establish a fluid flow. U.S. Pat. No. 4,533,347 exemplifies a conventional piggyback system which employs a controller to regulate the flow of fluids to the patient. The controller is positioned downstream of the fluid sources on the secondary fluid line and the combined fluid line to regulate flow in both lines simultaneously.

Although effective, conventional piggyback systems have nevertheless been found to be somewhat restrictive and cumbersome in that they rely on a check valve and the height differential of the fluid sources to ensure the desired delivery sequence of the treatment fluids despite the concurrent use of a pump or controller. Accordingly, it is an object of the present invention to provide a secondary treatment fluid administration system which is operable in cooperation with a conventional primary treatment fluid administration set, yet which is not restricted to only a sequential mode of fluid delivery to the patient. It is further an object of the present invention to diminish reliance on the height differential of the fluid sources as a mechanism for sequential fluid delivery. It is another object of the present invention to provide a secondary treatment fluid administration system which provides a driving force other than gravity or electro-mechanical pumping to convey fluid through the system. A final object of the present invention is to provide control of the secondary treatment fluid administration system by means independent of the primary set.

SUMMARY OF THE INVENTION

The present invention is a pumping system for administering a secondary treatment fluid to a patient intravenously wherein the system is structured to perform in cooperation with a primary treatment fluid administration set already in place. The present secondary treatment fluid pumping system comprises a self-contained pumping unit having a pumping chamber and a fluid reservoir integrated into a single compartment. A secondary fluid line extends from the pumping unit and joins with a primary fluid line of the primary set at a connector fitting. The fitting merges the two lines into an IV line which proceeds to the patient for intravenous delivery of the treatment fluids carried therein.

The junction of the primary and secondary fluid lines is downstream of any flow control devices on the primary fluid line. Control of the secondary pumping system is achieved independent of the primary set by means including a selectively positionable restriction mechanism on the secondary fluid line. A control assembly having a microprocessor in electrical communication with the restriction mechanism is provided for performing the control function of the system automatically. The control assembly includes push buttons for entering control commands to the microprocessor and a display for displaying operational data. Thus, the restriction mechanism is responsive to control commands inputted by the operator and stored in the microprocessor. When the restriction mechanism is in an extended position, the secondary fluid line is closed. When the restriction mechanism is in a retracted position the secondary fluid line is open and the secondary fluid is delivered to the patient. It is apparent that the microprocessor can be programmed so that at a predetermined point in time secondary fluid can be delivered to the patient for a predetermined duration and at the end of the predetermined duration fluid delivery can be automatically terminated.

Although the secondary treatment fluid pumping system is independently controllable, it is nevertheless designed to operate in concert with the primary set. Accordingly, the secondary pumping system is portable so that it may be placed in close proximity to the primary set during operation. The secondary pumping system is provided with means for removably affixing it to the stand of the primary set, or alternatively the system is provided with means for removably affixing it directly to the primary set. The pumping unit is preferably prefilled and presealed with a predetermined volume of treatment fluid to minimize fluid handling by the operator. The pumping unit can be fabricated from disposable materials thereby eliminating risks associated with refilling and reuse of the unit.

The secondary pumping system may be configured with a single pumping unit as described above or with a plurality of pumping units which operate in parallel. Each pumping unit of the multi-unit system has a secondary fluid line which connects into the system outlet line across a manifold. Control of the multi-unit system may be provided by a control assembly analogous to the above-described control assembly for the single pumping unit system.

The present invention is additionally a method for pumping secondary treatment fluid to a patient for intravenous infusion in cooperation with administration of a primary treatment fluid to the patient. The method comprises pumping the secondary treatment fluid from a reservoir which is structurally integral with the pumping chamber into a secondary fluid line. The secondary fluid is displaced through the secondary fluid line to a fitting which continuously merges the secondary fluid line and a primary fluid line into an IV line. The secondary fluid is then delivered to the patient intravenously across the IV line. The operator may either choose to deliver the secondary and primary fluids to the patient sequentially or deliver the secondary fluid to the patient coincident with simultaneous delivery of the primary fluid.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
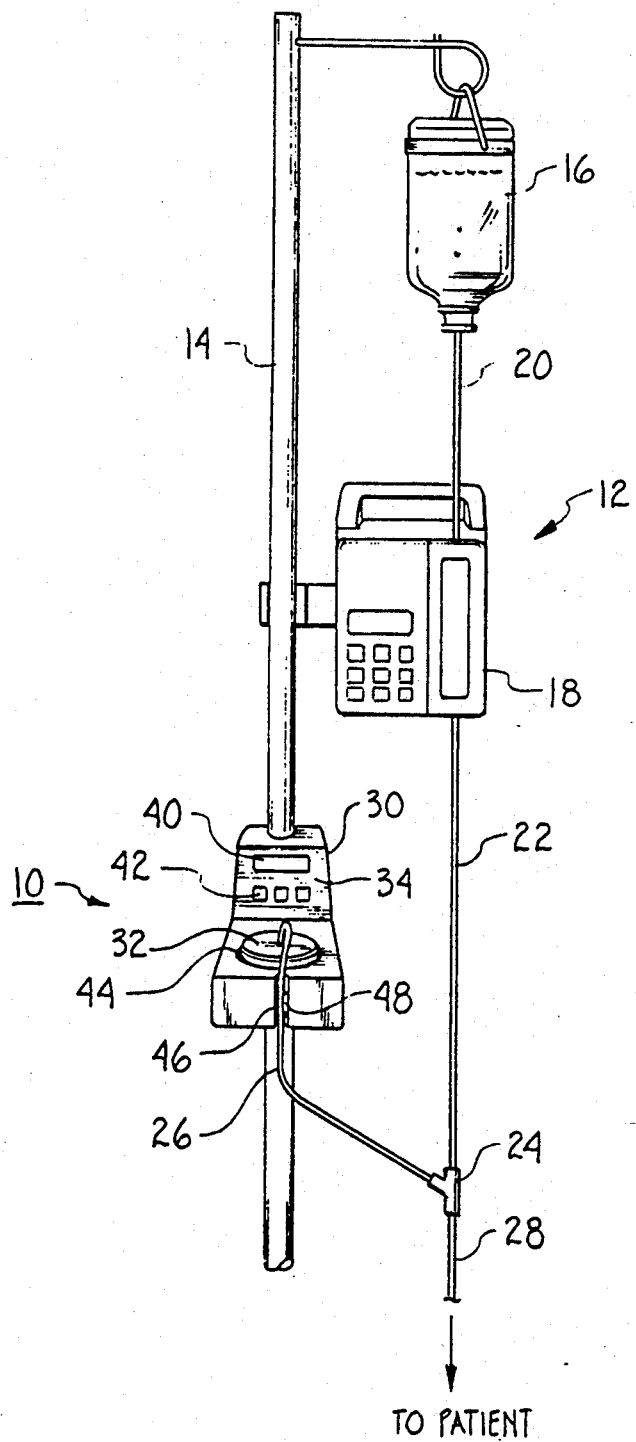
FIG. 1 is a perspective view of the secondary treatment fluid pumping system.

Referring initially to FIG. 1, the pumping system of the present invention for intravenously administering a secondary treatment fluid is shown assembled and generally designated as apparatus 10. Apparatus 10 is structured to perform in cooperation with a conventional primary treatment fluid administration set generally designated 12. Accordingly, apparatus 10 is shown mounted on an IV pole 14 of primary set 12 in close proximity thereto. Primary set 12 comprises a hangable primary treatment fluid bottle 16, a primary fluid control unit 18, which is typically either a controller or a pump, and two portions of tubing 20, 22. Upper tubing 20 leads from bottle 16 to primary control unit 18 and lower tubing 22 leads from bottle 16 to a connector fitting 24 of apparatus 10 which merges lower tubing 22 with an outlet tube 26 of apparatus 10 into a unified IV tube 28 to the patient.

Figure 2:
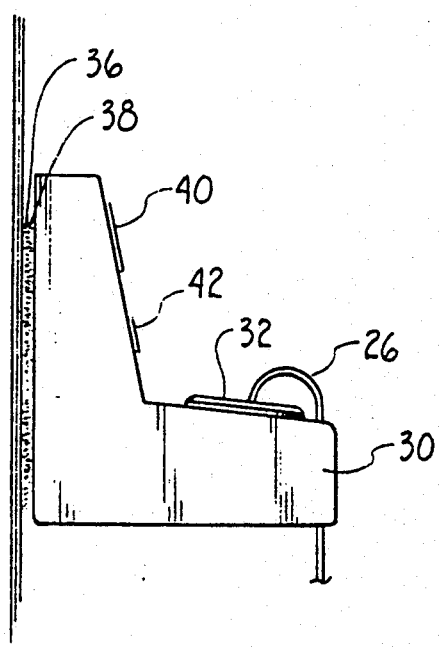
FIG. 2 is a side view of an embodiment for mounting the secondary treatment fluid pumping system.

In addition to fitting 24 and outlet tube 26, apparatus 10 further comprises a housing 30 which houses a self-contained pumping unit 32 and a control assembly 34. Housing 30 and its contents are relatively small and lightweight which renders them substantially portable for positioning near or adjacent associated primary set 12. As an alternative to the pole mounting of FIG. 1, FIG. 2 shows apparatus 10 mountable directly onto control unit 18 of primary set 12 by a releasable fastening means such as a pair of engagable Velcro strips 36, 38 affixed to control unit 18 and housing 30 respectively.

Referring back to FIG. 1, outlet tube 26, fitting 24, and IV tube 28 provide a continuous fluid pathway to the patient. Fitting 24 is preferably a conventional formed connector termed a Y-site connection which enables free unimpeded flow from outlet tube 26 and lower tubing 22 into IV tube 28. Housing 30 has on its face a visual display 40 and tactile push buttons 42 which enable operator interaction with control assembly 34. Housing 30 is further formed with a receptacle 44 shaped to receive self-contained pumping unit 32 and a slot 46 shaped to accommodate outlet tube 26 exiting a port connector 35 on unit 32 and a flow restrictor means, such as an occluder 48, which is shown mounted in housing 30.

Figure 3:
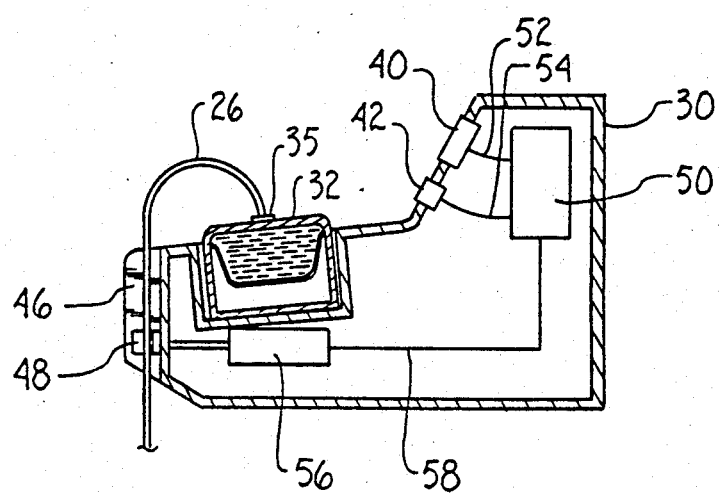
FIG. 3 is a cross sectional view of the secondary treatment fluid pumping system as seen along the line 2—2 in FIG. 1 with selected components shown schematically for clarity.

In FIG. 3 it will be seen that apparatus 10 includes a microprocessor 50 which is mounted inside housing 30 in a manner well known in the pertinent art. FIG. 3 also shows that microprocessor 50 is electrically connected to visual display 40 on housing 30 via electrical line 52 and electrically connected to tactile push buttons 42 on housing 30 via electrical line 54. Further, microprocessor 50 is electrically connected to an occluder drive mechanism 56 via an electrical line 58.

Figure 4:
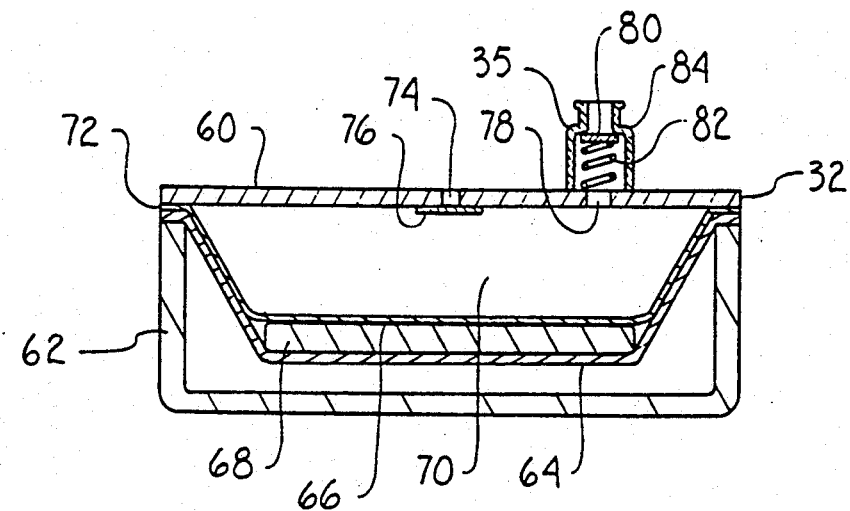
FIG. 4 is a detailed cross sectional view of the pumping chamber of the present invention as seen in FIG. 3.

Pumping unit 32 of apparatus 10 is, perhaps, best seen with reference to FIG. 4. There it will be seen that pumping unit 32 includes a plate 60 which covers a cup 62. A stretchable membrane 64 and a liner 66 enclose an impeller plate 68 and, together, create an expandable and contractible fluid pumping chamber 70 between liner 66 and plate 60. Pumping chamber 70 is preferably prefilled and presealed with the secondary treatment fluid, and accordingly functions simultaneously as a fluid reservoir for the secondary treatment fluid.

FIG. 4 shows stretchable membrane 64 and liner 66 are attached between plate 60 and cup 62 at the juncture 72 between liner 66 and cup 62. For purposes of the present invention, stretchable membrane 64 can be made of any suitable elastomeric material which will urge impeller plate 68 toward and into contact with the plate 60. Further, liner 66 can be made of any suitable material which is chemically and biologically compatible with the secondary treatment fluid medicament to be introduced into pumping chamber 70. The size of impeller plate 68 can vary to some degree, but it should be sufficiently large to maintain some stretch in membrane 64 and keep the force from membrane 64 on impeller plate 68 in its linear region, even when pumping chamber 70 has been completely collapsed. It is to be appreciated by one of ordinary skill in the art that with some design modification impeller plate 68 can be eliminated from pumping unit 32 and membrane 64 can be relied on as the sole pumping force on the secondary treatment fluid.

FIG. 4 also shows that plate 60 of pumping unit 32 is formed with an air vent 74 which is covered by a hydrophobic layer 76. Accordingly, when pumping chamber 70 is filled with fluid, air in chamber 70 can escape through air vent 74 without also losing fluid from the chamber 70. Plate 60 of pumping unit 32 is also formed with a fluid port 78 which is surrounded by port connector 35. A valve 80 is located between plate 60 and port connector 35. Which is urged by a spring 82 against the shoulder 84 of port connector 35. With this combination, fluid can be injected into the chamber 70 while valve 80 is depressed and, after chamber 70 has been filled, valve 80 will prevent pumping of fluid from the chamber 70 until port connector 35 is appropriately connected with outlet tube 26. It will be appreciated that various valving arrangements for pumping chamber 70 will suffice for purposes of the present invention.

Figure 5:
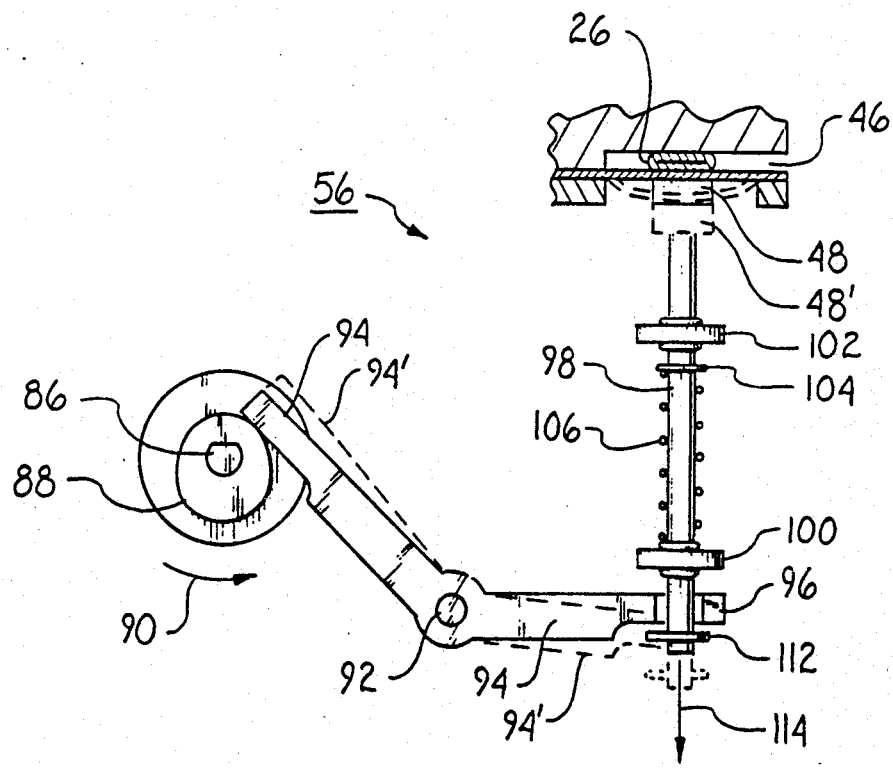
FIG. 5 is a top plan view of an embodiment for an occluder and occluder drive mechanism for the present invention shown in operative association with an IV tube.

Occluder drive mechanism 56 is shown in FIG. 5 to include a drive shaft 86 which is mounted on housing 30 for rotation by a motor (not shown). A cam 88 is fixedly attached to the drive shaft 86 for rotation with the drive shaft in the direction indicated by arrow 90. A pivot pin 92 is also mounted on housing 30 and an actuator arm 94 is attached to pin 92. Consequently, as cam 88 is rotated to urge against actuator arm 94, actuator arm 94 will pivot about the rotational axis of pivot pin 92. An end 96 of actuator arm is operatively engaged with a shaft 98 for operation of the occluder drive mechanism 56. Specifically, a bearing 100 and a bearing 102 are each mounted on housing 30 and shaft 98 is slidably mounted on bearings 100, 102. Further, shaft 98 is formed with a retainer ring 104 and a spring 106 is positioned around shaft 98 between the retainer ring 104 and the bearing 100. Occluder 48 is mounted on the end of shaft 98 as shown and will reciprocate with the movement of shaft 98.

FIG. 5 also shows that slot 46 creates a platen 108 and includes a flexible cover 110. As intended for the present invention, outlet tube 26 is positioned in slot 46 between platen 108 and flexible cover 110. As shown, occluder 48 is positioned against flexible cover 110 on the side of cover 110 opposite outlet tube 26. With this structure, a rotation of drive shaft 26 urges cam 88 against arm 94 to pivot the arm 94 around pivot pin 92 and into the position shown for arm 94'. As a result, end 96 of arm 94 urges against the abutment 112 on shaft 98 to move shaft 98 in the direction of arrow 114 and against the action of spring 106. Consequently, occluder 48 moves into the position shown for occluder 48' and the outlet tube 26 positioned in slot 46 will be opened for fluid flow. Further, rotation of shaft 86 will release shaft 98 from the influence of actuator arm 94 and allow spring 106 to urge occluder 48 into contact with tube 26 to prevent fluid flow through outlet tube 26.

OPERATION

In the operation of the secondary pumping system of the present invention, the operator first positions apparatus 10 in proximity to primary set 12, such as on the IV pole 14. The differential height between primary fluid bottle 16 and apparatus 10 is immaterial. Accordingly, the differential height between them may be positive, negative or zero.

A pumping unit 32, which has preferably been prefilled with a secondary treatment fluid to be infused, is then provided. Prefilling is typically performed at a remote site, e.g. the pharmacy of the hospital, and pumping unit 32 is transported to the location where the treatment fluid is to be infused to the patient. Specifically, prefilling is performed by attaching a syringe or some other device for pumping fluid to port connector 35 and injecting the secondary treatment fluid into reservoir/pumping chamber 70 of unit 32. As fluid is so injected impeller plate 68 is distanced from the plate 60 and chamber 70 expands under the influence of the injected fluid to stretch membrane 64. During the filling of chamber 70 any air in chamber 70 is vented through air vent 74. The result is that chamber 70 is filled only with the treatment fluid to be infused. As will be appreciated by the skilled artisan, several prefilled pumping units 32 can be stored on site before use, each unit 32 filled with a particular medicament which can be different from the medicaments used to fill the other pumping units 32.

Pumping unit 32 is connected in fluid communication with an IV tube 28 by attaching one end of IV tube 28 and one end of outlet tube 26 to Y-site connector fitting 24. The other end of outlet tube 26 is connected to port connector 35 which is a fixed calibrated orifice providing a fixed flow rate therethrough. The pumping unit 32 is then positioned in receptacle 44 and a portion of the outlet tube 26 which extends from port connector 35 is positioned in slot 46 for operative contact with occluder 48. The free end of IV tube 28 can then be attached to the patient. Importantly, upon placement of outlet tube 26 in slot 46 and into contact with occluder 48, occluder 48 initially occludes outlet tube 26.

Microprocessor 40 in housing 30 is programmed by the operator using tactile push buttons 42 of control assembly 34. According to this program, occluder 48 is activated to open outlet tube 26 at a preselected time and for a predetermined duration. Once past occluder 48, the secondary treatment fluid has an unobstructed flowpath to the patient across tubes 26, 28 and connector fitting 24.

Figure 6:
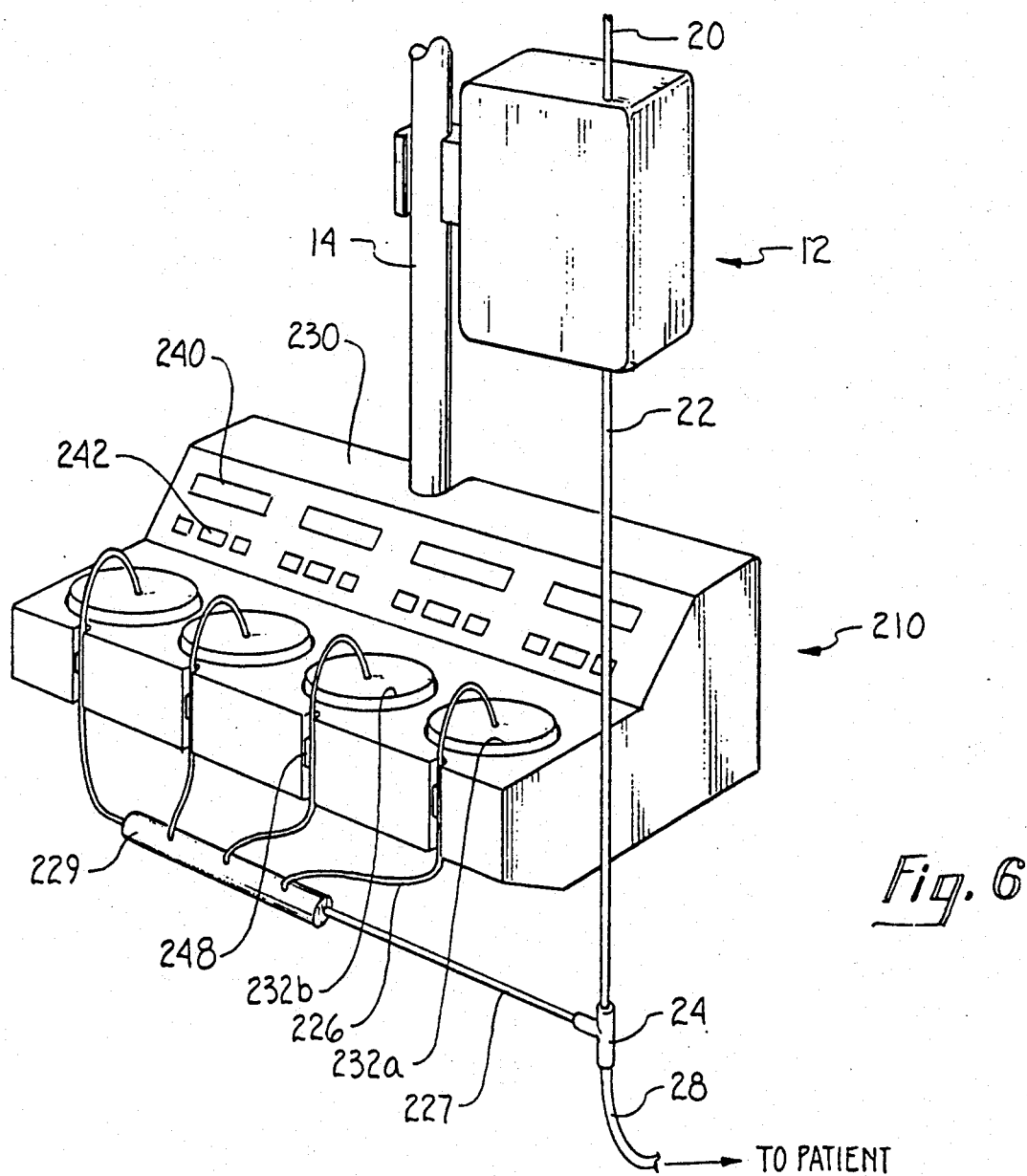
FIG. 6 is a perspective view of a second embodiment of the secondary treatment fluid pumping system.

FIG. 6 shows a second embodiment of the present invention wherein the secondary treatment fluid pumping system designated as apparatus 210 comprises a plurality of the above-described pumping units 232a, 232b and associated outlet tubes 226, occluders 248, and control assemblies contained within a single housing 230. Apparatus 210 is likewise designed to operate in cooperation with primary set 12. Secondary treatment fluid exit pumping units 232 into outlet tubes 226 which discharge into a combined tube 227 across a manifold 229. Combined tube 227 feeds into IV tube 28 across connector fitting 24 in the same manner as described above with respect to apparatus 10.

Although each tactile push button 242, each visual display 240, and each occluder 248 is separately operative through a central microprocessor (not shown) in housing 230 to independently control each pumping unit 232, the central microprocessor is nevertheless capable of coordinating the operation of a plurality of pumping units 232 and their respective occluders 248 to sequence their infusion of medical treatment fluids to the patient in accordance with a predetermined program. The central microprocessor is programmed by the operator via push buttons 242 to control the initiation and duration of infusion from a plurality of pumping units 232 mounted in housing 230. In this way, the multi-unit system provides a procedure for the timed sequencing of a plurality of prefilled pumping units 232.

While the particular secondary treatment fluid pumping system for infusing IV fluids to a patient as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A secondary pumping system for intravenous infusion of a secondary treatment fluid to a patient in combination with a primary treatment fluid administration set, said primary set having a primary fluid source, a primary fluid control unit and a primary fluid line providing a primary fluid pathway from said primary fluid control unit, said secondary pumping system comprising:

- a self-contained pumping unit having a secondary fluid reservoir and a secondary fluid pump integrated into a single compartment, wherein said secondary treatment fluid is pumped from said secondary fluid reservoir under the contractive force of a stretched elastic membrane, said elastic membrane forming a wall of said secondary fluid reservoir;
- a secondary fluid outlet port in said pumping unit;
- a secondary fluid line having two ends, a first end connected to said secondary fluid outlet port and a second end at a distance therefrom to form a secondary fluid pathway, said secondary fluid pathway mergable with said primary fluid pathway;
- means for restricting flow through said secondary fluid line;
- a unitary housing containing said flow restricting means and said pumping unit;
- a continuous fitting receiving said second end of secondary fluid line and further receiving said primary fluid line to merge said secondary fluid pathway and said primary fluid pathway; and
- a common fluid line providing a continuous common fluid pathway from said fitting to the patient.

2. A secondary pumping system as recited in claim 1 wherein said flow restricting means has an occluder extending from said housing to engage said secondary fluid line.

3. A secondary pumping system as recited in claim 1 wherein said unitary housing has a receptacle formed therein to removably retain said pumping unit.

4. A secondary pumping system as recited in claim 3 wherein said pumping unit is disposable.

5. A secondary pumping system as recited in claim 1 wherein said unitary housing is independently portable of said primary set.

6. A secondary pumping system as recited in claim 1 wherein said primary treatment fluid administration set further comprises a pole on which said primary set is mounted, said second set further comprising means for mounting said housing on said pole having said primary set mounted thereon.

7. A secondary pumping system as recited in claim 1 further comprising means for mounting said housing on said primary set.

8. A secondary pumping system as recited in claim 1 wherein said elastic membrane is an elastomeric membrane.

9. A secondary pumping system as recited in claim 1 further comprising a plurality of said secondary fluid pumping units, a plurality of said flow restricting means, and a plurality of branch lines at said first end of said secondary fluid line, each of said branch lines connected to each said secondary fluid outlet port of each said secondary pumping unit and each of said branch lines engaged by one of said flow restricting means.

10. A secondary pumping system as recited in claim 9 further comprising a control assembly in electrical communication with said plurality of flow restricting means.

11. A secondary pumping system as recited in claim 1 further comprising a control assembly in electrical communication with said flow restricting means.

12. A secondary pumping system as recited in claim 1 Wherein said compartment is prefillable and sealable with a predetermined volume of a secondary treatment fluid.

* * * * *